(12) United States Patent
Leahy

(10) Patent No.: US 10,631,735 B2
(45) Date of Patent: Apr. 28, 2020

(54) PHOTOACOUSTIC TOMOGRAPHY METHOD AND SYSTEM

(71) Applicant: NATIONAL UNIVERSITY OF IRELAND, GALWAY, Galway (IE)

(72) Inventor: Martin J. Leahy, Abbeyfeale (IE)

(73) Assignee: National University of Ireland, Galway, Galway (IE)

(*) Notice: Subject to any disclaimer, the term of this patent is extended or adjusted under 35 U.S.C. 154(b) by 608 days.

(21) Appl. No.: 15/111,911

(22) PCT Filed: Jan. 15, 2015

(86) PCT No.: PCT/EP2015/050698
§ 371 (c)(1),
(2) Date: Jul. 15, 2016

(87) PCT Pub. No.: WO2015/110349
PCT Pub. Date: Jul. 30, 2015

(65) Prior Publication Data
US 2016/0331240 A1 Nov. 17, 2016

(30) Foreign Application Priority Data
Jan. 23, 2014 (EP) .................. 14152357

(51) Int. Cl.
*A61B 5/00* (2006.01)
*A61B 5/1495* (2006.01)
(Continued)

(52) U.S. Cl.
CPC .............. *A61B 5/0095* (2013.01); *A61B 1/00* (2013.01); *A61B 5/1495* (2013.01);
(Continued)

(58) Field of Classification Search
CPC ... A61B 5/0095; A61B 5/7225; A61B 5/7278; A61B 1/00; A61B 5/4848;
(Continued)

(56) References Cited

U.S. PATENT DOCUMENTS 6,421,549 B1 * 7/2002 Jacques .............. A61B 5/14551
600/323
8,494,604 B2 * 7/2013 Li ........................ A61B 5/0059
600/310
(Continued)

FOREIGN PATENT DOCUMENTS

WO 2011/000389 A1 1/2011
WO 2011/038006 A1 3/2011
(Continued)

OTHER PUBLICATIONS

Jain et al, Review of Some Interesting Surface Plasmon Resonance-enhanced Properties of Noble Metal Nanoparticles and Their Applications to Biosystems, Feb. 12, 2007, Springer Science+Business Media LLC, vol. 2, 107-118.*
(Continued)

*Primary Examiner* — Sanjay Cattungal
(74) *Attorney, Agent, or Firm* — Studebaker & Brackett PC

(57) ABSTRACT

A method of calibrating a PAI system (401-413) is described. The method includes a signal processing unit (404) determining optical fluence at voxels within arteries of a human or animal, and interpolating from these measurements to provide a fluence map with a fluence value for all voxels of interest. The system (404) stores the fluence map for subsequent use in making PAI measurements. The arterial optical fluence may be determined on the basis that the arterial oxygen saturation ($SaO_2$) is the same throughout the arterial part of the circulation system.

19 Claims, 3 Drawing Sheets

(51) Int. Cl.
*A61B 1/00* (2006.01)
*A61B 5/1455* (2006.01)

(52) U.S. Cl.
CPC ........ *A61B 5/14552* (2013.01); *A61B 5/4848* (2013.01); *A61B 5/7225* (2013.01); *A61B 5/7278* (2013.01); *A61B 5/14551* (2013.01); *A61B 2560/0223* (2013.01); *A61B 2576/00* (2013.01)

(58) Field of Classification Search
CPC .............. A61B 5/14552; A61B 5/1495; A61B 2576/00; A61B 2560/0223; A61B 5/14551
See application file for complete search history.

(56) References Cited

U.S. PATENT DOCUMENTS

| | | | | |
|---|---|---|---|---|
| 2011/0079083 | A1* | 4/2011 | Yoo ..................... | G01S 7/52065 73/632 |
| 2011/0230760 | A1* | 9/2011 | Gambhir .............. | A61B 5/0071 600/431 |
| 2011/0270071 | A1* | 11/2011 | Furukawa ............ | A61B 5/0095 600/407 |
| 2013/0109941 | A1 | 5/2013 | Li et al. | |
| 2013/0109949 | A1* | 5/2013 | Li ..................... | G01N 21/1702 600/407 |
| 2014/0005544 | A1* | 1/2014 | Zalev .................. | A61B 5/0095 600/440 |
| 2014/0093150 | A1* | 4/2014 | Zalev .................. | G06T 7/0012 382/131 |

FOREIGN PATENT DOCUMENTS

| | | |
|---|---|---|
| WO | 2012/144395 A1 | 10/2012 |
| WO | 2013/134772 A2 | 9/2013 |

OTHER PUBLICATIONS

Sinex, Pulse Oximetry: Principles and Limitations, Jan. 1999, Smerican Journal of Emergency Medicine, vol. 17, 59-66.*
Hanning et al, Pulse oximetry:a practical review, Aug. 5, 1995, Fortnightly Review, vol. 311, 367-370.*
Jin et al, Ablation of Hypoxic Tumors with Dose-Equivalent Photothermal, but Not Photodynamic, Therapy Using a Nanostructured Porphyrin Assembly, Feb. 11, 2013, American Chemical Society, vol. 7, p. 2541-2550.*
Chien et al, Gold nanoparticles as high-resolution X-ray imaging contrast agents for the analysis of tumor-related micro-vasculature, 2012, Journal of Nanobiotechnology, vol. 10, p. 1-12.*
International Preliminary Report on Patentability and Written Opinion of the International Searching Authority dated Jul. 26, 2016, issued in corresponding International Application No. PCT/EP2015/050698.
International Search Report issued in PCT/EP2015/050698; dated Apr. 9, 2015.
Written Opinion issued in PCT/EP2015/050698; dated Apr. 9, 2015.
Jun Xia et al.; "Calibration-free quantification of absolute oxygen saturation based on the dynamics of photoacoustic signals"; Optics Letters; Aug. 1, 2013; pp. 2800-2803; vol. 38; No. 15; Optical Society of America.
B. T. Cox et al.; "The challenges for quantitative photoacoustic imaging"; Photons Plus Ultrasound: Imaging and Sensing 2009: The Tenth Conference on Biomedical Thermoacoustics, Optoacoustics, and Acousto-optics; Proc. of SPIE; pp. 717713 to 717713-9; vol. 7177.
Minghua Xu et al.; "Photoacoustic imaging in biomedicine"; Review of Scientific Instruments; 2006; pp. 041101-1 to 041101-22; vol. 77; American Institute of Physics.

* cited by examiner

PHOTOACOUSTIC TOMOGRAPHY METHOD AND SYSTEM

INTRODUCTION

Field of the Invention

The invention relates to photoacoustic tomography (PAT), sometimes alternatively referred to as "optoacoustic tomography (OAT)" or thermoacoustic tomography (TAT)" and perhaps more correctly photoacoustic imaging (PAI). In other terms, the invention applies to any form of tomography in which a photoacoustic source is produced inside the body, caused by thermal expansion, in turn caused by absorption of externally-applied electromagnetic waves. The term "PAI" or "photoacoustic imaging" is used in this specification.

PAI is an imaging technique which measures optical absorption, which is related to the optical absorption coefficient and the optical fluence. It has clinical applications in monitoring sub-surface tissue.

Current PAI systems provide mostly qualitative data and hence the applications are limited. This arises because in PAI the optical fluence needs to be known at each volume element (voxel). The paper Jun Xia et al "Calibration-free quantification of absolute oxygen saturation based on the dynamics of photoacoustic signals" OPTICS LETTERS (Vol. 38, No. 15/Aug. 1, 2013 describes an approach to addressing the problem of determining optical fluence by taking advantage of the dynamics in oxygen saturation ($sO_2$), where for each wavelength the ratio of photoacoustic amplitudes measured at different $sO_2$ states is utilized.

Other documents in this field are:
WO2011/038006 (Visen)
WO2011/000389 (Helmhno ltz)
B. T. Cox, J. G. Laufer, P. C. Beard: "The 1-15 challenges for quantitative photoacoustic imaging" In: 27 Feb. 2009, SPIE, PO Box 10 Bellinham Wash. 98227-0010 USA, XP040492002, DOI: 10.1117/12.806788
Xu Minghua, et. Al: "Photoacoustic imaging in biomedicine", Review of Scientific Instruments, AIP, Melville, N.Y., US, vol. 77, no. 4, 17 Apr. 2006, pages 41101-041101, XP012092965, ISSN: 0034-6748, DOI: 10.1063/1.2195024

The invention is directed towards providing an improved system and method for PAI.

SUMMARY OF THE INVENTION

This invention is aimed at making photoacoustic imaging (PAI) quantitative. Several attempts have been made to calibrate the PAI system, but this has proved elusive since the light fluence delivered to each voxel is unknown, hence the pressure amplitude detected may be indicative of a high concentration of absorber or due to a high light fluence. In order to disentangle these, the fluence at each voxel must be determined. The invention uses the knowledge that the content of the arterial blood is the same through the organism and hence it can be used as a local calibration "guide star" to calibrate the system for local fluence distribution. The absorption coefficient is known from the arterial oxygen saturation ($SaO_2$) and total haemoglobin (HbT). A calibrated system will be quantitative and hence has many applications in clinical, pre-clinical and fundamental science and discovery, including stem cell tracking, optimisation of cancer treatments and basic physiology studies.

According to the invention, there is provided a method of calibrating a PAI system, the method comprising the steps of:
determining optical fluence at voxels within arteries of a human or animal,
interpolating from said measurements to provide a fluence map with a fluence value for all voxels of interest, and
storing said fluence map for subsequent use in making PAI measurements,
wherein the arterial optical fluence is determined on the basis that the arterial oxygen saturation ($SaO_2$) is the same throughout the arterial part of the circulation system.

In one embodiment, the fluence map is generated for all wavelengths of interest.

In one embodiment, the method includes measuring $SaO_2$ in order to determine said optical fluence of voxels in the patient's arteries. In one embodiment, pulse oximetry is used to determine the $SaO_2$ value.

In one embodiment, the arterial optical fluence is determined on the basis that the arterial total haemoglobin fraction (HbT) is the same throughout the arterial part of the circulation system.

In one embodiment, the method includes measuring $SaO_2$ and HbT in order to determine said optical fluence of voxels. In one embodiment, pulse co-oximetry is used to determine the HbT value.

In one embodiment, the arterial oxygen saturation ($SaO_2$) is determined according to:

$$sO_2 = \frac{\varepsilon_{Hb}(\lambda_1) \cdot F(\lambda_1) - \varepsilon_{Hb}(\lambda_2) \cdot F(\lambda_2) \cdot \frac{P_0(\lambda_1, SO_2)}{P_0(\lambda_2, SO_2)}}{\frac{P_0(\lambda_1, SO_2)}{P_0(\lambda_2, SO_2)} \cdot F(\lambda_2)(C_{HbT} \cdot \varepsilon_{HbO_2}(\lambda_2) - \varepsilon_{Hb}(\lambda_2)) + F(\lambda_1)(\varepsilon_{Hb}(\lambda_1) - C_{HbT} \cdot \varepsilon_{HbO_2}(\lambda_1))}$$

In one embodiment, the calibration uses the small path length change in arteries and/or arterioles to isolate absorption due to only arterial blood.

In one embodiment, the pulse oximetry uses the small path length change in arteries and/or arterioles to isolate absorption due to only arterial blood.

In one embodiment, the arterioles are in the finger.

In another aspect, the invention provides a PAI system comprising a processor adapted to perform calibration in a method as defined above in any embodiment.

In one embodiment, the system is adapted to perform assessment of tumour treatment potential by determining vascularity such as perfused vessel density, and borders.

In one embodiment, the system is adapted to perform assessment of tumour treatment potential by identifying the volume and borders of hypoxic regions which may not respond to cancer agents, such those designed to produce singlet oxygen as part of the treatment mechanism.

In one embodiment, the system is adapted to perform assessment of drug delivery and distribution in an animal or human by using dyes or fluorophores to label the drugs. In one embodiment, the system is adapted to perform assessment of drug delivery and distribution in an animal or human by using nanoparticles to label the drugs.

In one embodiment, the system is adapted to perform assessment of drug delivery and distribution in an animal or human by using nanoparticles to label the drugs.

In one embodiment, the system is adapted to perform assessment of drug delivery and distribution or biodistribution (distribution of cells in an animal or human) in an animal or human by using high aspect ratio or other nanoparticles to label the drugs, thereby permitting deeper imaging. In one embodiment, the system is adapted to perform assessment of biodistribution (distribution of cells in an animal or human) for stem cell therapy.

In one embodiment, the system is adapted to perform assessment of biodistribution (distribution of cells in an animal or human) for stem cell therapy using dyes/fluorophores/nanoparticles to label the cells.

In one embodiment, the system comprises an endoscope for use in said calibration

DETAILED DESCRIPTION OF THE INVENTION

The invention will be more clearly understood from the following description of some embodiments thereof, given by way of example only with reference to the accompanying drawings in which:—

It is known that a pulse oximetry tool can be used to non-invasively determine arterial oxygen saturation ($SaO_2$), and this is the same everywhere within the arterial side of the circulation system.

A tomographic system of the invention divides the tissue into volume elements (voxels) and measures the acoustic pressure generated at each voxel within the arteries in the field of view. From this, and knowledge that the $SaO_2$ is the same at all of these locations, it can readily calculate the fluence at all voxels within the arteries. From this it interpolates to calculate a map of fluence at all voxels. Once it has the fluence map it is calibrated, and can give the true concentration of any absorbing chromophore in any voxel in the field of view.

The system of the invention performs the following steps:
(a) Acquire the raw photoacoustic pressure measurement at each voxel.
(b) In the region of interest, find the nearest artery/arteriole.
(c) Calculate the local fluence from the measurement in (b). Since the concentration of oxy and deoxy-haemoglobin is the same everywhere in the arterial system (can be easily measured on the finger) the absorption coefficient of arterial blood can be calculated with a pulse oximeter measurement.
(d) Apply the local fluence as a calibration factor to give the concentration of any absorber in the voxel with known absorption coefficient within a region expected to have the same fluence (e.g. 10×10×2 mm).
(e) Repeat (a) to (d) for all wavelengths of interest (as determined from the absorption spectra of the analytes (absorbers).

The system calculates a fluence map from measurements at the arteries distributed through the volume and applies that as the calibration factor. In the first instance the arteries are manually identified and the fluence for each voxel is interpolated from those identified. This could be automated using the pulsing nature of arterial blood.

For calibration, the system determines the optical fluence at voxels within arteries of a human or animal. It does this by measuring the acoustic pressure pulse amplitude. This is proportional to the energy deposited in the voxel. Energy deposited is essentially the absorption coefficient times fluence. The absorption coefficient is known from $SaO_2$ and HbT, and knowing these are the same everywhere in the arterial system, the system of the invention can determine a fluence map for all voxels in the arterial 'tree'. It interpolates to estimate the fluence in the remaining voxels.

Figure 1:
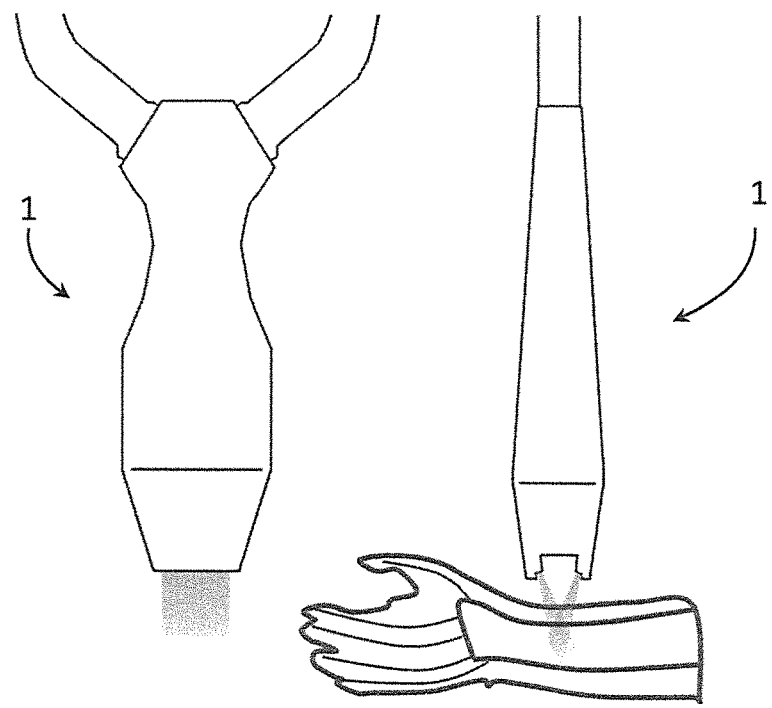
FIG. 1 shows an ultrasound probe in use.

Referring to the drawings FIG. 1 shows use of a clinical ultrasound probe 1 which is operated in reflection mode. Instead of ultrasound output, the acoustic signal is generated by short (typically <10 ns) laser pulses which are absorbed in the tissue. The instrument comprises a tuneable laser system for generating light pulses of approximately 50 mJ in 10 ns at a variation of wavelengths. The light pulses are absorbed by all arteries in the illuminated field. The arterial blood will rise in temperature by a few mK and, since the pulse time is too short for thermodilution, will release an acoustic vibration (pressure wave) with a spectrum of frequencies in the MHz range. This pressure variation will travel isotropically in all directions and may be detected in any direction. We assume here that it is detected in reflection mode similar to a clinical ultrasound instrument.

The oxygen saturation ($sO_2$) is the fraction of total haemoglobin (HbT) bound to oxygen:

$$sO_2 = \frac{HbO_2}{HbO_2 + Hb} = \frac{HbO_2}{HbT}$$

The remaining fraction is haemoglobin which is not bound to oxygen. The arterial oxygen saturation ($SaO_2$) is the fraction of total haemoglobin in the arterial blood bound to oxygen. $SaO_2$ can be readily measured at the finger with a pulse oximeter (called $SpO_2$ just to indicate pulse measurement) and is the same at all locations in the arterial system. The Beer-Lambert law (or Beer's law) is the linear relationship between absorbance and concentration of an absorbing species:

$$A = \alpha_\lambda x c$$

where A is the measured absorbance, $\alpha_\lambda$ is a wavelength-dependent absorption coefficient, x is the path length, and c is the analyte concentration,

OR $$dI = -c\sigma_a I dx$$

where dI is the measured variation in transmitted intensity, I is the incident intensity, $\sigma_a$ is a wavelength-dependent absorption cross-section, dx is the path length change, and c is the species concentration.

Figure 2:
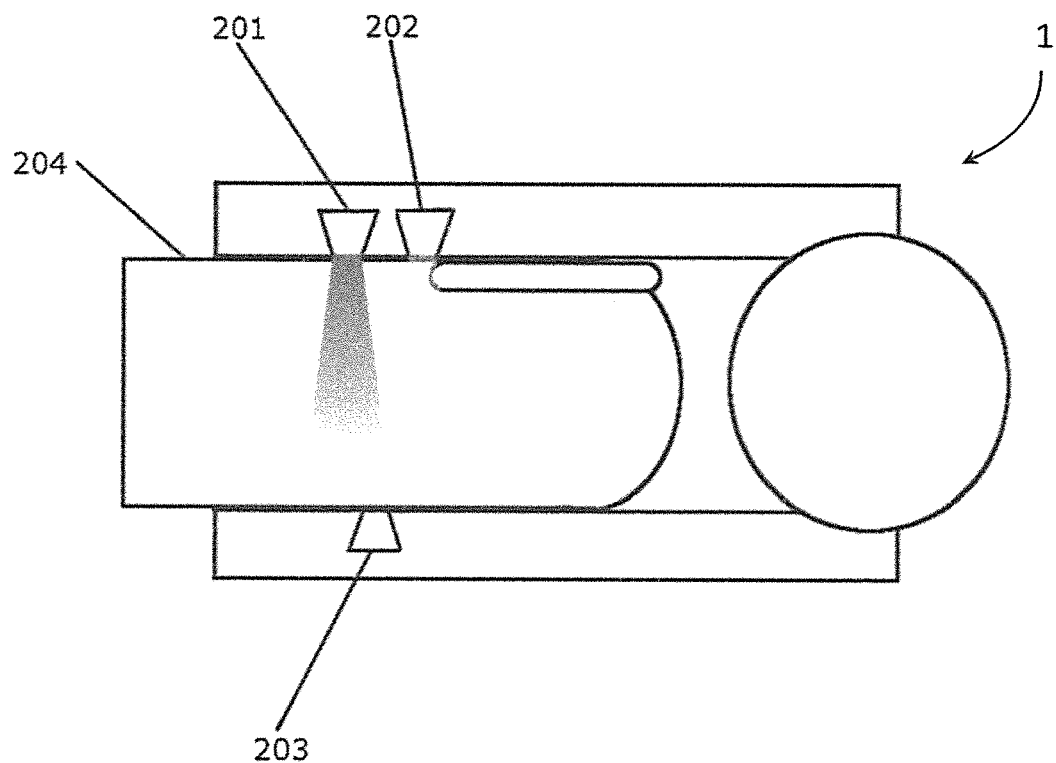
FIG. 2 shows a system for determining arterial oxygen saturation $SaO_2$.

Referring to FIG. 2, red light of wavelength 660 nm (201) and mean intensity $I_R$ falls on a detector 203 having passed through the finger 204 of a patient in critical care. Infrared light 202 of wavelength 960 nm and mean intensity $I_{IR}$ falls on the same detector having traveled the same path. The 660 nm light has a peak-to-peak intensity variation of $dI_R$, while that at 960 nm varies by $dI_{IR}$. The red and infrared light is pulsed on and off alternatively so that they can be detected on the same detector-amplifier combination and de-multiplexed later to provide the red and infrared component signals. The cardio-synchronous variation in blood volume leads to a varying optical path length. The Beer-Lambert law dictates that the received intensity is proportional to the varying optical path length. The Beer-Lambert law dictates that the received intensity is proportional to the absorption coefficient of the substance through which it passes, in this case blood. Each translucent substance has an absorption spectrum which is the variation in absorption with wavelength. The pulse oximeter operates by using the small path length change in the arteries of the finger caused by the cardiac pulse (only present on the arterial side) to isolate absorption due to only the arterial blood. The instrument filters the alternating signals of amplitude $dI_R$ & $dI_{IR}$ and normalises them by $I_R$ & $I_{IR}$.

$$\frac{(dI/I)_R}{(dI/I)_{IR}} = \frac{SaO_2\sigma_{ao,R} + (1-SaO_2)\sigma_{ar,R}}{SaO_2\sigma_{ao,IR} + (1-SaO_2)\sigma_{ar,IR}}$$

$$SaO_2 = \frac{\sigma_{ar,R} - \frac{(dI/I)_R}{(dI/I)_{IR}} \cdot \sigma_{ar,IR}}{-\sigma_{ao,R} + \sigma_{ar,R} + (\sigma_{ao,IR} - \sigma_{ar,IR}) \cdot \frac{(dI/I)_R}{(dI/I)_{IR}}}$$

Figure 3:
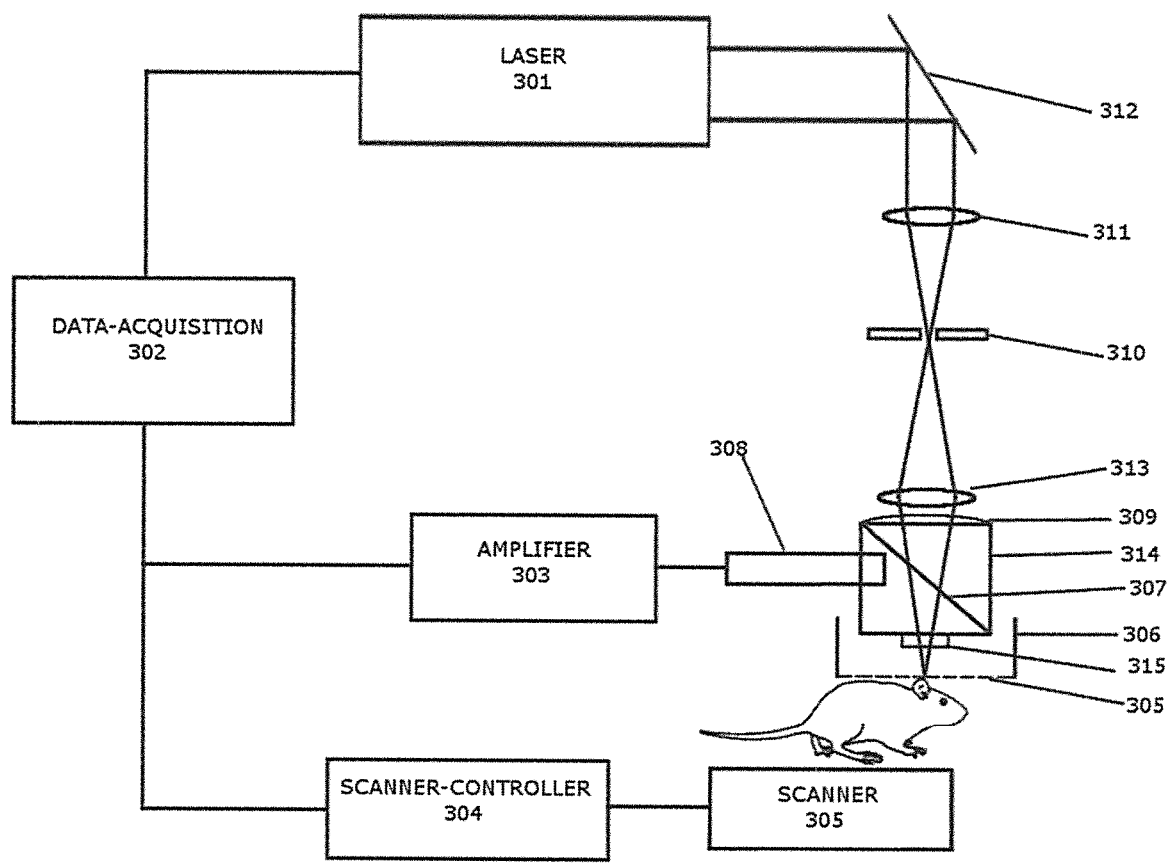
FIG. 3 shows a pre-clinical photoacoustic configuration.

FIG. 3 shows a pre-clinical PAI system. A laser 301 provides a pulsed irradiation source. The laser beam is redirected by a mirror 312 and focused by a lens 311 through a pinhole 310, where it is spatially filtered, and then focused by an objective lens 313. Ultrasonic focusing is achieved by the use of an acoustic lens 315. The objective lens and the ultrasonic transducer are confocally configured via a correction lens 309, a right angle prism 314, and a silicon oil layer 307. The sample 304 is separated from the acoustic lens by a plastic membrane 305 and a water tank 306. Acoustic signals are generated in the sample 304 target site, due to the temperature rise associated with the absorption of pulsed laser energy, focused from the objective lens 313. The detected acoustic data is sent from the transducer (308), via an amplifier 303, to a data acquisition and signal processing unit 302, where it is converted into an image using image reconstruction techniques. 3D images are generated by raster scanning in the transverse plane, which is achieved by moving the sample 304 on a scanner 305 (a two-dimensional moving platform). The scanner is controlled by a scanner controller 304, which is controlled by the data acquisition device 302

Figure 4:
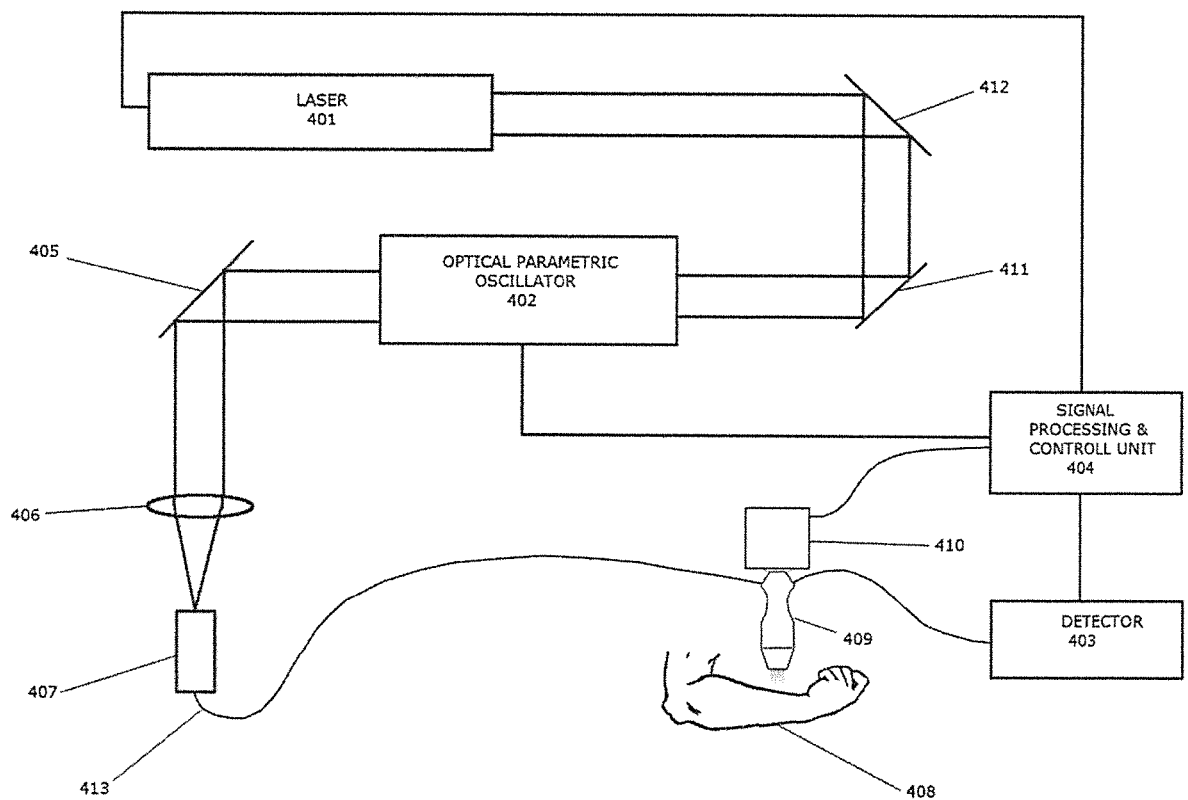
FIG. 4 shows a system for both pre-clinical and clinical use.

FIG. 4 shows the use of a PAI system with clinical and pre-clinical applications. The probe shown in this system is a photoacoustic probe 409, i.e. one in which the laser source and ultrasonic transducer detectors are housed in the same unit. Pulsed optical energy is generated by a laser 401, and directed via mirrors 412, 411 to an optical parametric oscillator (OPO) 402, which is a device used to convert the incident light into a different wavelength within a given range, specified by a control unit 404. The laser output from the OPO 402 is passed through a lens 406, which focuses the light onto a fibre optic coupling 407, which is connected to a fibre optic cable 413, and then to the probe 409. Acoustic signals are generated in the site of interest in a patient 408, due to the absorption of pulsed laser energy delivered by the probe. The acoustic information is relayed, via an ultrasound detector 403, to a signal processing and control unit 404, where the data is processed into an image by a reconstruction algorithm. 3D images can be obtained by moving the probe across the surface of the tissue with a stepper motor 410.

The signal processing and control unit 404 causes the OPO 402 to deliver light pulses at 750 nm for one scan and at 795 nm (isobestic for Hb and $HbO_2$) for another scan and 1064 nm for a third scan (other wavelengths could be used). A voltage related to sound pressure is detected by the ultrasound detector 403 and fed to the signal processing and control unit 404 where the below equations can be used to estimate blood $sO_2$ from two or more of these wavelengths. Since all of these wavelengths are strongly absorbed by blood, the ultrasound transducer 403 will detect strong signals from voxels containing blood and the signal processing and control unit 404 will be able to render this data as images of the arterial and venous trees within the volume imaged. Hence the arterial tree can be segmented out and can act as a distributed calibration reference for the fluence throughout the tissue. This will be used as described below to provide a fluence map and hence calibrated distribution of $sO_2$ or other absorber of interest.

The local fluence (F) is proportional to the initial pressure rise ($p_0$) and inversely proportional to the product of the Grüneisen coefficient ($\Gamma$) and the optical absorption coefficient ($\mu_a$), thus:

$$F = \frac{p_0}{\Gamma \mu_a}$$

Since the Grüneisen coefficient ($\Gamma$) is independent of wavelength it cancels in ratiometric measurements (i.e. we are generally dividing the measured $p_0$ at one wavelength by that at another wavelength) or we can use spectrometrically measured $\Gamma$ [Proc. SPIE 8581, Photons Plus Ultrasound: Imaging and Sensing 2013, 858138 (Mar. 4, 2013); doi: 10.1117/12.2004117] or can assume values for fat, skin, muscle and blood from the literature. Hence in most cases we can view $p_0$ as the simple product $\mu_a F$. For visible and near-infrared light, the main absorbers in a blood vessel are oxy- ($HbO_2$) and deoxy-haemoglobin (Hb). Therefore, the optical absorption coefficient at wavelength $\lambda_1$ and $sO_2$ can be expressed as:

$$\mu_a(\lambda_1; sO_2) = \ln(10)[C_{HbT} \cdot sO_2 \cdot \varepsilon_{HbO2}(\lambda_1) + C_{HbT} \cdot (1-sO_2) \cdot \varepsilon_{Hb}(\lambda_1)]$$

where $C_{HbT}$ is the total hemoglobin concentration, and $\varepsilon HbO_2$ and $\varepsilon_{Hb}$ are the molar extinction coefficients of $HbO_2$ and Hb, respectively, all of which are known a priori, or can be determined using pulse (co-)oximetry or a lab co-oximeter via arterial blood sampling. Hence the system can calculate the fluence at each voxel and produce a 3D fluence map. From this the system can determine $sO_2$ in other capillaries, venules and veins as well as any analyte with a significant and distinct absorption spectrum.

Where the fluence is not known and where the path lengths are well known (photoacoustic microscopy) Wang et al 2006 (Xueding Wang, Xueyi Xie, Geng Ku, Lihong V. Wang, George Stoica, 2006. "Noninvasive imaging of haemoglobin concentration and oxygenation in the rat brain using high-resolution photoacoustic tomography" Biomed Opt. 11 (2), 024015; doi:10.1117/1.2192804) give these equations for HbT and $sO_2$, which attempt to minimize the impact of the unknowns:

$$sO_2 = \frac{[HbO_2]}{[HbO_2]+[Hb]} = \frac{\mu_a^{\lambda_2}\varepsilon_{Hb}^{\lambda_1} - \mu_a^{\lambda_1}\varepsilon_{Hb}^{\lambda_2}}{\mu_a^{\lambda_1}\Delta\varepsilon_{Hb}^{\lambda_2} - \mu_a^{\lambda_2}\Delta\varepsilon_{Hb}^{\lambda_1}}$$

$$HbT = [HbO_2]+[Hb] = \frac{\mu_a^{\lambda_1}\Delta\varepsilon_{Hb}^{\lambda_2} - \mu_a^{\lambda_2}\Delta\varepsilon_{Hb}^{\lambda_1}}{\varepsilon_{Hb}^{\lambda_1}\varepsilon_{HbO_2}^{\lambda_2} - \varepsilon_{Hb}^{\lambda_2}\varepsilon_{HbO_2}^{\lambda_1}}$$

However, from the equation for $\mu_a(\lambda_1; sO_2)$ it follows [2013/Vol. 38, No. 15/OPTICS LETTERS 2801] that the photoacoustic pressure amplitude ratio for two wavelengths, ($\lambda_1, \lambda_2$) is thus:

$$p_0(\lambda_1, sO_2) = CHbT[sO_2 \times \varepsilon HbO_2(\lambda_1) + (1-sO_2) \times \varepsilon Hb(\lambda_1)]F(\lambda_1)$$

$$p_0(\lambda_2, sO_2) = CHbT[sO_2 \times \varepsilon HbO_2(\lambda_2) + (1-sO_2) \times \varepsilon Hb(\lambda_2)]F(\lambda_2)$$

which can be re-arranged to give sO$_2$ in any vessel thus:

$$SO_2 = \frac{\varepsilon_{Hb}(\lambda_1) \cdot F(\lambda_1) - \varepsilon_{Hb}(\lambda_2) \cdot F(\lambda_2) \cdot \frac{P_0(\lambda_1, SO_2)}{P_0(\lambda_2, SO_2)}}{\frac{P_0(\lambda_1, SO_2)}{P_0(\lambda_2, SO_2)} \cdot F(\lambda_2)(C_{HbT} \cdot \varepsilon_{HbO_2}(\lambda_2) - \varepsilon_{Hb}(\lambda_2)) + F(\lambda_1)(\varepsilon_{Hb}(\lambda_1) - C_{HbT} \cdot \varepsilon_{HbO_2}(\lambda_1))}$$

Once the fluence is determined as set out above, the system can be calibrated and many applications become possible for clinical, pre-clinical (and other studies). These include the assessment of biodistribution (distribution of cells or drugs in an animal or human) for stem cell therapy and the identification of hypoxic regions in tumours.

Stem cell therapies have the potential to generate/regenerate tissues or whole organs. Cells may be taken from the same patient to avoid biocompatibility, rejection issues. Progress is limited due to lack of methods to determine the biodistribution within an animal or human. Currently, this mainly relies on euthanizing the animal and histological examination. This provides one time point and, since this is a dynamic process, it is unclear where this time point is within that process (peak, before peak after peak . . . ). In vivo monitoring of stem cell distribution in living animals and humans would permit longitudinal studies showing the time course and facilitate optimised treatment regimens. Furthermore, stem cells are proposed as a mechanism of drug delivery since they will in some circumstances have the ability to locate tumours. PAI imaging for stem cell tracking will likely require cell labelling with nanoparticles or dyes or fluorophores.

Drug resistance is a major problem with cancer treatments. Many cancer agents try to generate singlet oxygen within the tumour and the singlet oxygen kills the tumour cells. A substantial proportion of resistant tumours are found to have hypoxic regions (lack oxygen) and hence have low potential to produce singlet oxygen. This may be because the tumour has grown rapidly (uncontrollably) and many cells are too far from the blood vessels for oxygen delivery. Imaging of the vasculature and its sO$_2$ content will facilitate the identification of tumours which will be resistant to these treatments and hence save these patients the trauma of those chemotherapy sessions.

A calibrated system will also tremendously aid fundamental science and discovery, by providing calibrated reliable data relating to many things including oxygen supply and consumption. For example, it could provide much more direct quantitative imaging of brain function and better knowledge of the parts of the brain involved in various functions and importantly the relative contribution (or load) from various parts of the brain.

The invention is not limited to the embodiments described but may be varied in construction and detail. For example the processing for calibration or for any of the analysis techniques may be performed by a remote processor linked to the photoacoustic detector, rather than the local signal processor.

The invention claimed is:

1. A method of calibrating a photoacoustic imaging system, the method being performed by a photoacoustic imaging system including
   a radiation source,
   a photoacoustic detector, and
   a processor,
   the method steps comprising
   determining arterial optical fluence at voxels within arteries of a human or animal by exposure to the radiation source and measurement of the exposure by the photoacoustic detector,
   interpolating by the processor from said determined arterial optical fluence on a basis that arterial oxygen saturation SaO$_2$ and arterial total haemoglobin fraction HbT are the same throughout an arterial part of a human or animal circulation system to provide a fluence map with a fluence value for all voxels of interest, and
   storing said fluence map for subsequent use by the photoacoustic imaging system in making photoacoustic imaging measurements.

2. The method of calibrating a photoacoustic imaging system as claimed in claim 1, wherein the fluence map is generated for all wavelengths of interest.

3. The method of calibrating a photoacoustic imaging system as claimed in claim 1, wherein the method includes measuring SaO$_2$ in order to determine said arterial optical fluence of voxels in the patient's arteries.

4. The method of calibrating a photoacoustic imaging system as claimed in claim 1, wherein the method includes measuring SaO$_2$ in order to determine said optical fluence of voxels in the patient's arteries, and wherein pulse oximetry is used to measure SaO$_2$.

5. The method of calibrating a photoacoustic imaging system as claimed in claim 1, wherein the method includes measuring SaO$_2$ and HbT in order to determine said arterial optical fluence of voxels.

6. The method of calibrating a photoacoustic imaging system as claimed in claim 1, wherein the method includes measuring SaO$_2$ and HbT in order to determine said arterial optical fluence of voxels, and wherein pulse co-oximetry is used to determine the HbT value.

7. The method of calibrating a photoacoustic imaging system as claimed in claim 1, wherein the method includes measuring SaO$_2$ in order to determine said optical fluence of voxels in the patient's arteries, and wherein pulse oximetry is used to measure the SaO$_2$ value, and wherein the calibration uses the small path length change in arteries and/or arterioles to isolate absorption due to only arterial blood.

8. The method of calibrating a photoacoustic imaging system as claimed in claim 1, wherein the method includes measuring SaO$_2$ in order to determine said optical fluence of voxels in the patient's arteries, and wherein pulse oximetry is used to measure the SaO$_2$ value, and wherein the pulse oximetry uses the small path length change in arteries and/or arterioles to isolate absorption due to only arterial blood.

9. The method of calibrating a photoacoustic imaging system as claimed in claim 1, wherein the method includes measuring SaO$_2$ in order to determine said optical fluence of voxels in the patient's arteries, and wherein pulse oximetry is used to measure the SaO$_2$ value, wherein the calibration uses the small path length change in arteries and/or arterioles to isolate absorption due to only arterial blood, and wherein the arterioles are in the finger.

10. The photoacoustic imaging system as claimed in claim 1, wherein the system is configured to perform assessment of drug delivery and distribution in an animal or human by using nanoparticles to label the drugs.

11. A photoacoustic imaging system comprising a radiation source, a photoacoustic detector, and a processor configured to perform calibration in a method comprising the steps of:

determining arterial optical fluence at voxels within arteries of a human or animal by exposure to the radiation source and measurement of the exposure by the photoacoustic detector, interpolating by the processor from said determined arterial optical fluence on a basis that arterial oxygen saturation $SaO_2$ and arterial total haemoglobin fraction HbT are the same throughout an arterial part of a human or animal circulation system to provide a fluence map with a fluence value for all voxels of interest, and storing said fluence map for subsequent use by the photoacoustic imaging system in making photoacoustic imaging measurements.

12. The photoacoustic imaging system as claimed in claim 11, wherein the system is configured to perform assessment of tumour treatment potential by determining vascularity including perfused vessel density, and borders.

13. The photoacoustic imaging system as claimed in claim 11, wherein the system is configured to perform assessment of tumour treatment potential by identifying the volume and borders of hypoxic regions which may not respond to cancer agents, including those designed to produce singlet oxygen as part of the treatment mechanism.

14. The photoacoustic imaging system as claimed in claim 11, wherein the system is configured to perform assessment of drug delivery and distribution in an animal or human by using dyes or fluorophores to label the drugs.

15. The photoacoustic imaging system as claimed in claim 11, wherein the system is configured to perform assessment of drug delivery and distribution in an animal or human by using nanoparticles to label the drugs.

16. The photoacoustic imaging system as claimed in claim 11, wherein the system is configured to perform assessment of drug delivery and distribution or biodistribution in an animal or human by using high aspect ratio or other nanoparticles to label the drugs, thereby permitting deeper imaging.

17. The photoacoustic imaging system as claimed in claim 11, wherein the system is configured to perform assessment of biodistribution for stem cell therapy.

18. The photoacoustic imaging system as claimed in claim 11, wherein the system is configured to perform assessment of biodistribution for stem cell therapy using dyes and/or fluorophores and/or nanoparticles to label the cells.

19. The photoacoustic imaging system as claimed in claim 11, wherein the system comprises an endoscope for use in said calibration.

* * * * *